United States Patent [19]

Paul et al.

[11] Patent Number: 5,068,471
[45] Date of Patent: Nov. 26, 1991

[54] CONTINUOUS TELOMERIZATION PROCESS

[75] Inventors: Norbert Paul, Altötting; Rudolf Huber, Garching; Ingolf Mielke, Burgkirchen, both of Fed. Rep. of Germany

[73] Assignee: Hoechst Aktiengesellschaft, Frankfurt am Main, Fed. Rep. of Germany

[21] Appl. No.: 630,178

[22] Filed: Dec. 19, 1990

[30] Foreign Application Priority Data

Dec. 21, 1989 [DE] Fed. Rep. of Germany ....... 3942316

[51] Int. Cl.$^5$ .................. C07C 17/24; C07C 17/26; C07C 17/28; C07C 19/07
[52] U.S. Cl. .................................... 570/139; 570/137
[58] Field of Search ......................................... 570/139

[56] References Cited

U.S. PATENT DOCUMENTS 2,694,701 11/1954 Blum et al. ........................... 570/139
3,142,708 7/1964 Young .................................. 570/139

FOREIGN PATENT DOCUMENTS 1443517 7/1973 Fed. Rep. of Germany .
1535408 12/1978 United Kingdom .

OTHER PUBLICATIONS

Bloechl, W., *Chem. Abs.* 65:20005f (1966) (=DE 1,443,517=Fr. 1,434,643).

*Primary Examiner*—J. E. Evans

[57] ABSTRACT

A process for continuous telomerization is described, in which at least one telogenic compound and at least one taxogenic compound are reacted at from 40° to 150° C. under a pressure of from 0.1 to 3 MPa in the presence of at least one catalyst in an elongate cylindrical reaction space. After it has left the reaction space, the reaction mixture is separated, for example by distillation, the desired higher-molecular telomers are discharged as the bottom product, and the undesired low-molecular telomerization products are stripped off over the top, condensed and recycled into the process in a first circulation. In a second circulation, a part of the reaction mixture is taken off towards the end of the reaction space and reintroduced into the initial part of the reaction space. This allows an improved space-time yield and a better selection of defined product cuts.

5 Claims, No Drawings

CONTINUOUS TELOMERIZATION PROCESS

DESCRIPTION

The invention relates to a process for continuous telomerization, in which a telogenic compound, which is liquid under the reaction conditions, is reacted with at least one taxogenic compound having an ethylenic double bond and 2 to 4 carbon atoms, at from 40° to 150° C. under a pressure of from 0.1 to 3 MPa in the presence of at least one catalyst in an elongate cylindrical reaction space.

Telomerization or telomerization reaction is the description of a process in which, according to the current state of knowledge, a telogenic compound AX decomposes under the action of light or heat into two fragments A and X, to which compounds having a polymerizable, in most cases ethylenic double bond, called "taxogenic compounds" below, are added once or several times one after the other, in accordance with the following reaction equation:

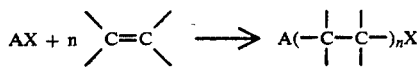

A number of catalysts are known which accelerate this reaction, so that lower activation temperatures suffice.

Amongst the many possible telomerization reactions which are possible with taxogenic compounds which contain an ethylenic double bond, those have gained industrial interest which lead to the formation of short- and medium-chain, highly fluorinated compounds, the telogenic compounds used being advantageously perfluoroalkyl iodides and the taxogenic compounds used being ethylene or highly fluorinated alkylenes such as tetrafluoroethene, chlorotrifluoroethene or hexafluoropropene.

German Auslegeschrift 1,443,517 (C.A. Volume 65, 1966, No. 20005f) has disclosed a process in which perfluoroiodoalkanes as the telogenic compounds are reacted in the gaseous state with tetrafluoroethene or hexafluoropropene at temperatures of from 250° to 800° C., and under pressures from 2 mm Hg to 5 atmospheres with residence times of less than 1 hour in a tubular reaction space. The desired telomeric compounds are condensed out of the gas mixture and the uncondensed gas mixture is recirculated again after making up the telogenic and the taxogenic compound(s). This process does not give good space-time yields, especially at low pressures, and also the application of the said temperatures, especially at pressures above normal atmospheric pressure, involves considerable risk of a spontaneous uncontrollable decomposition in the case of thermally unstable taxogenic compounds such as tetrafluoroethene.

As already mentioned above, a fair number of catalysts for the telomerization reaction are known, discontinuous processes (boiling under reflux with solvents, single or batchwise charging of an autoclave) are as a rule employed in the examples of the corresponding publications. As a representative of a number of similar publications, the process described in British Patent 1,535,408 for the preparation of perfluoroiodide telomers by reacting perfluoroalkyl iodides with tetrafluoroethene at an elevated pressure and an elevated temperature in the liquid phase in the presence of di-(alkylphenyl) peroxydicarbonates as catalysts forming free radicals may be mentioned here, wherein the homologous perfluoroalkyl iodides having 1 to 5 carbon atoms are separated off after the reaction by fractional distillation and recycled into the process. The process proceeds under pressures of from 5 to 17 atmospheres gauge and at temperatures from 45° to 100° C. and can be carried out discontinuously, semicontinuously (with discontinuous take-off of the reaction mixture) and also fully continuously. More detailed data on the fully continuous procedure are not given, and the examples are exclusively carried out discontinuously.

As compared with the process known from German Auslegeschrift 1,443,517 (C.A. Volume 65, 1966, 20005f), this has the substantial advantage that it can be operated at a lower temperature in the liquid phase, whereby the risk of spontaneous decomposition of thermally unstable taxogenic compounds such as tetrafluoroethene is substantially reduced but, in the more economical, continuous procedure in an elongate, cylindrical reaction space, the space-time yields of, in particular, medium-chain telomers leave something to be desired, as the following comparative experiments show.

A process has now been found which makes more advantageous space-time yields possible and allows improved control of the reaction with a view to products of defined composition, in particular a defined carbon chain length.

The novel process for continuous telomerization of at least one telogenic compound, which is liquid under the reaction conditions, with at least one taxogenic compound having an ethylenic double bond and 2 to 4 carbon atoms, at a temperature of from 40° to 150° C. and under a pressure of from 0.1 to 3 MPa in the presence of at least one catalyst in an elongate cylindrical reaction space, separation of the reaction mixture after the telomerization reaction has ended and the mixture has left the reaction space, and discharge of the desired higher-molecular telomerization products as well as recycle of the undesired lower-molecular telomerization products and of the unconverted starting substances and reintroduction thereof to the telomerization reaction in a first circulation, the consumed starting substances being made up, comprises discharging a part of the essentially liquid reaction mixture from that half of the reaction space which is the second in the direction of flow and reintroducing it, without separating off constituents, in a second circulation into that half of the reaction space which is the first in the direction of flow, 20 to 90% of the total length of the reaction space being located between the discharge and the introduction.

A fair number of compounds are suitable as the telogenic compounds which are liquid under the reaction conditions, for example alkanols having 1 to 4 carbon atoms, especially if highly fluorinated ethylenic compounds are employed as the taxogenic compounds. Preferably, the telogenic compounds used are highly fluorinated alkyl iodides of the formula

in which R is H, F or

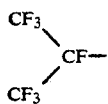

and n is a number from 1 to 6, telomeric compounds which contain not more than 6 carbon atoms being used preferably. In many cases, mixtures of different telomeric compounds are used.

From the large number of suitable taxogenic compounds which contain an ethylenic double bond and 2 to 4 carbon atoms, the following are used preferably: ethylene, vinyl fluoride, vinylidene fluoride, chlorotrifluoroethylene and especially hexafluoropropene and tetrafluoroethene.

The process according to the invention is carried out at a temperature of from 40° to 150° C. Below 40° C., the reaction proceeds in general too slowly even if catalysts are added, and temperatures of 150° C. are admittedly possible but in general not required; in addition, they represent an increasing safety risk and an additional cost which is in general unnecessary. Preferably, the process is operated at temperatures of from 50° to 100° C.

The novel process runs under a pressure of from 0.1 to 3 MPa. In principle, application of a pressure below 0.1 MPa is also possible, but this gives unnecessarily unfavorable space-time yields. The maximum pressure to be applied depends on the stability and reactivity of, in particular, the taxogenic compounds, a pressure above 3 MPa in general not being required. Preferably, the process is operated under a pressure of from 0.3 to 2.5 MPa. When tetrafluoroethene is used as the taxogenic compound, a maximum pressure of 2.5 MPa should appropriately not be exceeded, for safety reasons.

The telomerization reaction is carried out in the presence of at least one catalyst. Suitable catalysts are peroxidic compounds which decompose into free radicals and which, at the selective reaction temperature, have a decomposition half-life in the range from about 3 to 60 minutes, and also metal salts by themselves, in a mixture with one another and in a mixture with amine compounds as metal ion/amine systems. Examples which may be mentioned of peroxidic compounds decomposing into free radicals are peroxyalkanecarboxylic acids whose hydrogen atoms can be wholly or partially substituted by fluorine or chlorine, anhydrides and esters thereof, such as tertiary-butyl perpivalate, peroxyalcohols such as ditertiary-butyl hydroperoxide or peroxy ethers such as ditertiary-butyl peroxide, and also aliphatically or aromatically substituted peroxydicarbonates. Examples of suitable metal salts are the halides, phosphates, carbonates, nitrates, sulfates, cyanides, hydrides and ethoxides of metals of groups Ia, IIa, IIIa, IIIb to VIb and VIIIb. Such metal salts, in particular the halides, are used together with primary, secondary or tertiary alkylamines, cycloalkylamines, arylamines or alkanolamines and also heterocyclic amines, for example pyridine, mixtures of metal salts with one another also being used. Azo compounds decomposing into free radicals are also used, for example azoisobutyric acid dinitrile. The quantity of the catalyst, relative to the quantity of telogenic compound employed, is in general 0.05 to 1% by weight, preferably 0.1 to 0.5% by weight.

An elongated cylindrical reaction space is used for the process according to the invention, advantageously a tube which preferably has a length/internal diameter ratio of from 500 to 20,000, especially from 1,000 to 10,000. The free passage cross-section of the reaction space is not critical, and in general those reaction spaces (tubes) will be used which have a free passage cross-section of from about 1 to about 50 cm$^2$. The arrangement of the reaction space is likewise not critical; it can be arranged vertically, horizontally or inclined at a certain angle to the horizontal, and it can be a tube in superposed windings or in a zig-zag form.

The taxogenic compound is fed into the start of the reaction space; the telogenic compound(s) liquid under the reaction conditions is or are fed at a distance of from 0 to 25% of the total length of the reaction space away from the start of this reaction space, this feeding advantageously taking place downstream of the reintroduction of the reaction mixture circulating in accordance with the invention. The telogenic compound(s) can be temperature-controlled before entry into the reaction space, for example for conversion into the liquid state. The telogenic compounds can be fed at various points of the reaction space, but feeding at one point is in general sufficient. The catalyst is advantageously introduced into the reaction space together with the telogenic compounds, dissolved or suspended in the latter.

After it has left the reaction space, the reaction mixture is separated. This can advantageously be carried out by distillation under elevated pressure, normal atmospheric pressure or reduced pressure. A device, which enables a differential pressure to be maintained, for example a pressure-reducing valve, is advantageously arranged between the reaction space and the distillation equipment. The pressure in the reaction space, indicated above, is the maximum pressure prevailing there. As a rule, it is measured at the start of the reaction space. The reaction mixture is separated into the desired, as a rule higher-boiling telomerization products which remain in the bottom during the distillation, and into the undesired, lower-boiling telomerization products and the unchanged starting substances which go over the top in the distillation. If a distillation is carried out, the pressure in the distillation apparatus is, as far as possible, selected such that a bottom temperature of from 50° to 150° C. is established. Bottom temperatures above about 170° C. should not be exceeded, since higher temperatures frequently lead to undesired decomposition of the telomers. The bottom product is cooled and collected in a stock tank. Even though mixtures of different compounds are as a rule obtained in the telomerization, the bottom product can be used for many applications without further purification. If necessary, it can be further separated into its components by known methods.

The undesired (lower-molecular) telomers, separated off from the desired telomers, and unchanged starting products are cooled, the low-molecular telomers and the telogenic compound(s) used as starting products being condensed. Advantageously, the quantity of the telogenic compound(s) consumed for producing the desired telomers and the catalysts are added to this condensate, and this liquid is fed back into the reaction space in a first circulation, as described above. The compounds which are non-condensable in the condensation of the undesired telomers are, if appropriate after purification and/or separation and re-use of the taxogenic compound(s) contained therein, released as waste gas into the atmosphere.

At least such a rate of taxogenic compound(s) as is necessary for producing the desired telomers on the basis of stoichiometry is fed into the reaction space. Advantageously, a small molar excess is used, the rate fed being set such that at most 10% thereof appears in the non-condensable fractions of the separated reaction mixture.

The rate of new telogenic compound, which is liquid under the reaction conditions, which is fed to the first circulation which contains the undesired telomers which have been separated off, should advantageously be set such that, after constant conditions have been established in the continuous process, a calculated mean residence time in the reaction space of from 5 to 50 minutes results, allowing only for the compounds fed as liquids. In this range, good results are in general obtained, and the process is preferably carried out with a calculated mean residence time of from 10 to 30 minutes.

According to the invention, a part of the substantially liquid reaction mixture is discharged from that half of the reaction space which is the second in the direction of flow and, without separation of constituents, reintroduced in a second circulation into that half of the reaction space which is the first in the direction of flow. The discharge point should be located 10 to 45%, preferably 20 to 40%, of the total length of the reaction space away from the end thereof, and the reintroduction point should be located 0 to 35%, preferably 0 to 10%, of the total length of the reaction space away from the start thereof. The distance from the discharge to the reintroduction point should be 20 to 90% of the total length of the reaction space. If the distance is less than 20%, the effect according to the invention is then only small. At a distance of more than 90%, the utilization of the catalyst frequently turns out to be too unfavorable. Preferably, a distance of from 40 to 80% of the total length of the reaction space is maintained.

The second circulation is advantageously accomplished by means of a tube with a pump which delivers the reaction mixture taken off to the reintroduction point. The free passage cross-section of the circulation tube can be of the same magnitude as the free passage cross-section of the reaction space, or somewhat smaller or somewhat larger. Any pressure-raising pump which can be used for delivering a gas/liquid mixture is in principle suitable as the pump, for example a diaphragm pump, piston pump or gear pump.

The rate of the reaction mixture discharged and fed back in the second circulation should preferably be 0.5 to 50 times the total of the rates of the products reintroduced in the first circulation and of the newly added starting substances. The process according to the invention can readily be carried out within this range. Particularly good results are obtained when 2 to 20 times this rate is used.

Good results are also obtained when the ratio of the product rate obtained in the first circulation as a condensate from the top product of the distillation to the total of the rates of the newly fed starting substances for the telomerization reaction (telogenic and taxogenic compounds) is 10 to 50.

As already mentioned at the outset, the process according to the invention allows higher space-time yields and a better selection of defined product cuts. The expenditure on apparatus for carrying out the process according to the invention is small.

The comparative experiments and examples which follow are intended to illustrate the invention in more detail.

COMPARATIVE EXPERIMENT A

The following apparatus is used:
a vessel with a stirrer is connnected via a metering pump to a reaction tube which has a length/internal diameter ratio of 8,080. One end of the reaction tube is connected to an inlet for a pressurized gas serving as the taxogenic compound, and a line with a pressure control valve leads from the other end of the reaction tube to a distillation column which has a separation effect of 15 theoretical plates. A temperature control liquid flows around the reaction tube and is in turn circulated via a thermostat and a pump. The bottom of the distillation column has an orifice for discharging the product collected there, which runs through a product cooler into a product receiver. The top product from the distillation column runs through a distillate cooler in which the major part thereof is condensed. The non-condensable fractions are released into the atmosphere via a cold trap. The condensate runs into a condensate receiver which is in turn connected via a valve to the abovementioned vessel with a stirrer. This vessel can be temperature-controlled, has approximately 5 times the capacity of the reaction tube and contains one device each for adding liquid telogenic starting compound and for adding catalyst.

For carrying out the comparative experiment, a solution which, at the start of the experiment, contains 0.018% by weight of a peroxidically decomposing catalyst which has a decomposition half-life of 1.2 minutes at 90° C., dissolved in perfluoroethyl iodide, is prepared in the vessel with a stirrer. 7.70 parts by weight of this solution are introduced per hour via the metering pump into the reaction tube whose temperature is, controlled at 92° C. and into which, in addition, 0.20 part by weight per hour of tetrafluoroethylene is introduced under pressure.

The pressure at the start of the reaction tube is 1.4 MPa. After a mean residence time of about 16 minutes, the reaction mixture leaves the reaction tube and is fed via the pressure control valve into the distillation column. After constant conditions have been established, the bottom temperature is 150° C. 0.31 part by weight per hour of a product is then taken off from the bottom of the distillation column via the cooler into the product receiver; based on analysis by gas chromatography, this product contains

| | | |
|---|---|---|
| $C_6F_{13}I$ | 37.7% | = 0.117 part by weight/hour |
| $C_8F_{17}I$ | 39.8% | = 0.123 part by weight/hour |
| $C_{10}F_{21}I$ and higher | 22.5% | = 0.070 part by weight/hour |

The top product from the distillation column gives, after condensation in the distillate cooler, 7.54 parts by weight per hour of a liquid which essentially contains the starting product $C_2F_5I$ and low telomers $C_4F_9I$ and $C_6F_{13}I$. This liquid is passed into the condensate receiver and from there into the vessel with a stirrer. In the latter, 0.15 part by weight/hour of $C_2F_5I$ and 0.0014 part by weight/hour of catalyst are added, again giving a solution which contains 0.018% by weight of catalyst and which is fed again into the reaction tube. In the cold trap, 0.035 part by weight/hour is condensed out of the non-condensable fractions from the top product of the distillation column, and the remaining waste gas is released into the atmosphere.

EXAMPLE 1

The procedure followed is as indicated in Comparative Experiment A, but the reaction tube contains, at a distance of 32.7% of the total length of the reaction tube away from the end of this tube, a branching tube which has the same cross-section as the reaction tube and is connected to the start of the reaction tube via a circulation pump which has a controllable output and delivers against the direction of flow of the mixture in the reaction tube. The distance of the reintroduction of the branch tube is thus 0% of the total length of the reaction tube away from the start of this tube. The start and end of the reaction tube are here meant in the direction of flow of the mixture in this tube. The output of the circulation pump is adjusted such that 63 parts by weight/hour of the reaction mixture are circulated. 67.3% of the total length of the reaction tube are located between the discharge from the reaction tube and the introduction of the circulated part of the mixture into the reaction tube. The ratio of the product rate recycled in the first circulation (7.54 parts by weight/hour) to the total of the rate of the newly fed starting substances (0.20+0.15=0.35 part by weight/hour) is 21.5. The rate of the reaction mixture discharged and reintroduced in the second circulation (63 parts by weight/hour) is 8 times that of the mixture of reintroduced products reintroduced into the reaction tube (7.54 parts by weight/hour) and newly added starting substances (0.35 part by weight/hour).

After constant conditions have been established, the pressure at the start of the reaction tube is 1.75 MPa and the bottom temperature of the distillation column is 158° C. In the product receiver, 0.32 part by weight/hour of a product is obtained which contains, according to analysis by gas chromatography:

| $C_6F_{13}I$ | 21.7% = 0.069 part by weight/hour |
| $C_8F_{17}I$ | 50.0% = 0.160 part by weight/hour |
| $C_{10}F_{21}I$ and higher | 28.3% = 0.091 part by weight/hour |

0.023 Part by weight/hour is condensed out of the fractions, non-condensable in the distillate cooler, from the top product of the distillation column, and the remaining waste gas is released into the atmosphere.

As will be seen, a 30.1% higher proportion than in comparative experiment A of the desired telomers having 8 and more carbon atoms is obtained under the same conditions, with a reduced rate of waste gas. The increase in the proportion of $C_8F_{17}I$ is 30.1%.

COMPARATIVE EXPERIMENT B

In the same apparatus as described in comparative experiment A, 7.70 parts by weight/hour of the catalyst solution, which contains 0.018% by weight of a peroxidically decomposing catalyst having a decomposition half-life of 1.2 minutes at 90° C., are introduced via the metering pump into the reaction tube which is at a controlled temperature of 94° C. and into which in addition 0.29 part by weight/hour of tetrafluoroethylene is introduced under pressure. The pressure at the start of the reaction tube is 1.4 MPa. After a mean residence time of about 16 minutes, the reaction mixture leaves the reaction tube and is fed via the pressure control valve into the distillation column. After constant conditions have been established, the bottom temperature is 155° C. 0.40 Part by weight/hour of a product is then taken off from the bottom of the distillation column via the cooler into the product receiver; based on analysis by gas chromatography, this product contains

| $C_6F_{13}I$ | 36.2% = 0.145 part by weight/hour |
| $C_8F_{17}I$ | 37.5% = 0.150 part by weight/hour |
| $C_{10}F_{21}I$ and higher | 26.3% = 0.105 part by weight/hour |

After condensation in the distillate cooler, the top product from the distillation column gives 7.51 parts by weight per hour of a liquid which essentially contains the starting product $C_2F_5I$ and low telomers $C_4F_9I$ and $C_6F_{13}I$. This liquid is passed into the condensate receiver and from there into the vessel with a stirrer. In the latter, 0.18 part by weight/hour of $C_2F_5I$ and 0.0014 part by weight/hour of catalyst are added, again giving a solution which contains 0.018% by weight of catalyst and which is fed again into the reaction tube. In the cold trap, 0.074 part by weight/hour is condensed out of the non-condensable fractions from the top product of the distillation column, and the remaining waste gas is released into the atmosphere.

EXAMPLE 2

The procedure followed is as indicated in comparative experiment B, the branched tube described in Example 1 with a circulation pump on the reaction tube being used. The output of the circulation pump is adjusted such that 33.6 parts by weight/hour of the reaction mixture are circulated. After constant conditions have been established, the pressure at the start of the reaction tube is 1.6 MPa and the bottom temperature of the distillation column is 153° C. In the product receiver, 0.505 part by weight/hour of a product is obtained which, according to an analysis by gas chromatography, contains:

| $C_6F_{13}I$ | 37.6% = 0.190 part by weight/hour |
| $C_8F_{17}I$ | 37.0% = 0.187 part by weight/hour |
| $C_{10}F_{21}I$ and higher | 25.4% = 0.128 part by weight/hour |

0.019 Part by weight/hour is condensed out of the fractions, non-condensable in the distillate cooler, from the top product of the distillation column, and the remaining waste gas is released into the atmosphere. The ratio of the product rate recycled after the distillation in the first circulation and reintroduced (7.47 parts by weight/hour) to the total of the rates of the newly fed starting substances (0.29+0.23=0.52 part by weight/hour) is 14.4. The rate of the reaction mixture discharged and reintroduced in the second circulation (33.6 parts by weight/hour) is 4.2 times that of the mixture, introduced into the reaction tube, of reintroduced products (7.47 parts by weight/hour) and newly added starting substances (0.52 part by weight/hour).

As will be seen, a 23.5% higher proportion than in comparative experiment B of the desired telomers having 8 and more carbon atoms is obtained under the same conditions, with a reduced rate of waste gas. The increase in the proportion of $C_8F_{17}I$ is 24.7%.

We claim:

1. A process for continuous telomerization of at least one telogenic compound, which is liquid under the reaction conditions, with at least one taxogenic compound having an ethylenic double bond and 2 to 4 carbon atoms, at a temperature of from 40° to 150° C. and under a pressure of from 0.1 to 3 MPa in the presence of at least one catalyst in an elongate cylindrical reaction space, separation of the reaction mixture after the telomerization reaction has ended and the mixture has left the reaction space, and discharge of the desired higher-molecular telomerization products as well as recycle of the undesired lower-molecular telomerization products and of the unconverted starting substances and reintroduction thereof to the telomerization reaction in a first circulation, the consumed starting substances being made up, which comprises discharging a part of the essentially liquid reaction mixture from that half of the reaction space which is the second in the direction of flow and reintroducing it, without separating off constituents, in a second circulation into that half of the reaction space which is the first in the direction of flow, 20 to 90% of the total length of the reaction space being located between the discharge and the introduction.

2. The process as claimed in claim 1, wherein the rate of the reaction mixture discharged and fed back in the second circulation is 0.5 to 50 times the total of the rates of the products reintroduced in the first circulation and of the newly added starting substances.

3. The process as claimed in claim 1, wherein the elongate cylindrical reaction space has a length/diameter ratio of from 500 to 20,000.

4. The process as claimed in claim 1, wherein the ratio of the product rate recycled in the first circulation to the total of the rates of the newly fed starting substances for the telomerization reaction is 10 to 50.

5. The process as claimed in claim 1, which is operated under a pressure of from 0.3 to 2.5 MPa.

* * * * *